US011649470B2

(12) United States Patent
Behkish et al.

(10) Patent No.: US 11,649,470 B2
(45) Date of Patent: May 16, 2023

(54) FEED CONTROL IN CONVERSION OF BIOMASS INTO HYDROCARBON FUELS AND CHEMICALS

(71) Applicant: ExxonMobil Technology and Engineering Company, Annandale, NJ (US)

(72) Inventors: Arsam Behkish, Flemington, NJ (US); Giovanni Pilloni, Jersey City, NJ (US); Kelsey M. McNeely, Lambertville, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 27 days.

(21) Appl. No.: 16/870,914

(22) Filed: May 9, 2020

(65) Prior Publication Data
US 2021/0017548 A1 Jan. 21, 2021

Related U.S. Application Data

(60) Provisional application No. 62/876,006, filed on Jul. 19, 2019.

(51) Int. Cl.
*C12P 7/10* (2006.01)
*C12M 1/00* (2006.01)

(52) U.S. Cl.
CPC ............ *C12P 7/10* (2013.01); *C12M 43/02* (2013.01); *C12M 45/06* (2013.01); *C12P 2201/00* (2013.01)

(58) Field of Classification Search
CPC ....... C12P 7/10; C12P 2201/00; C12M 43/02; C12M 45/06
USPC ......................................................... 435/165
See application file for complete search history.

(56) References Cited

U.S. PATENT DOCUMENTS

| | | | | |
|---|---|---|---|---|
| 2006/0263860 A1* | 11/2006 | Vermerris | ............... | C12P 19/02 435/165 |
| 2008/0286870 A1* | 11/2008 | Viitanen | .................... | C12P 7/10 435/471 |
| 2011/0003352 A1* | 1/2011 | Retsina | .................... | C08H 8/00 435/136 |
| 2014/0163210 A1* | 6/2014 | Retsina | .................... | C13K 1/04 530/507 |
| 2014/0182582 A1* | 7/2014 | Retsina | ............... | C08B 37/0057 127/37 |
| 2015/0167969 A1* | 6/2015 | Retsina | .................... | C08H 8/00 110/346 |
| 2015/0184260 A1* | 7/2015 | Retsina | ................ | C13K 13/002 435/165 |
| 2015/0275237 A1* | 10/2015 | Retsina | .................... | C12P 7/18 435/158 |
| 2017/0002387 A1* | 1/2017 | Retsina | ................... | C12P 19/02 |

FOREIGN PATENT DOCUMENTS

WO WO 2015/026660 * 2/2015

OTHER PUBLICATIONS

Erdei et al., "Separate hydrolysis and co-fermentation for improved xylose utilization in integrated ethanol production from wheat meal and wheat straw", Biotechnology for Biofuels (2012), vol. 5, No. 12, pp. 1-13.
Nielsen et al., "Sequential targeting of xylose and glucose conversion in fed-bath simultaneous saccharification and co-fermentation of steam-pretreated wheat straw for improved xylose conversion to ethanol", Bioenergy. Res. (2017), vol. 10, pp. 800-810.
Nielsen et al., "Prefermentation improves ethanol yield in separate hydrolysis and confermentation of steam-pretreated wheat straw", Sustainable Chemical Processes (2016), vol. 4, No. 10, pp. 1-12.
Davis et al., "Process Design and Economics for the Conversion of Lignocellulosic Biomass to Hydrocarbons:Dilute-Acid and Enzymatic Deconstruction of Biomass to Sugars and Biological Conversion of Sugars to Hydrocarbons", Technical Report NREL/TP-5100-60223, Oct. 2013.
Kumar et al., "Recent updates on different methods of pretreatment of lignocellulosic feedstocks: a review", Bioresources and Bioprocessing (2017), vol. 4, No. 7, pp. 1-19.

(Continued)

*Primary Examiner* — Jennifer M. H. Tichy
(74) *Attorney, Agent, or Firm* — Shook, Hardy & Bacon, LLP (57) ABSTRACT

The present disclosure relates to processes for producing hydrocarbon fuels from lignocellulosic biomass. A process may include introducing biomass to a pretreatment system, and a first separation system forming a pentose-rich stream and a pentose-lean stream. The pentose-lean stream may be introduced to a hydrolysis system forming a hydrolysate and the hydrolysate introduced to a second separation system forming a hexose-rich stream and a lignin stream. Additionally, at least one of the pentose-rich stream or the hexose-rich stream may be introduced to a bioreactor containing microorganisms configured to produce hydrocarbon fuels. Additionally, the present disclosure also relates to systems for the production of hydrocarbon fuels. A system may include a pretreatment system, a first separation system, a hydrolysis system, a second separation system, and one or more bioreactors. Alternatively a system may include a pretreatment system, a hydrolysis system, a sugar separation system, and one or more bioreactors.

23 Claims, 2 Drawing Sheets

(56) References Cited

OTHER PUBLICATIONS

Jonsson et al., "Pretreatment of lignocellulose: Formation of inhibitory by-products and strategies for minimizing their effects", Bioresource Technology, (2016), vol. 199, pp. 103-112.
Weil et al., "Removal of Fermentation Inhibitors Formed during Pretreatment of Biomass by Polymeric Adsorbents", Ind. Eng. Chem. Res. (2002), vol. 41, No. 24, pp. 6132-6138.
Jonsson et al., "Bioconversion of lignocellulose: inhibitors and detoxification", Biotechnology for Biofuels (2013), vol. 6, No. 16, pp. 1-10.
Nichols et al., "Bioabatement to Remove Inhibitors from Biomass-Derived Sugar Hydrolysates", Applied Biochemistry and Biotechnology (2005), vol. 121-124, pp. 379-390.

* cited by examiner

FEED CONTROL IN CONVERSION OF BIOMASS INTO HYDROCARBON FUELS AND CHEMICALS

CROSS-REFERENCE TO RELATED APPLICATIONS

This application claims priority to U.S. Provisional Application No. 62/876,006 filed Jul. 19, 2019, which is herein incorporated by reference in its entirety.

FIELD OF THE INVENTION

The present disclosure relates to methods and systems for converting biomass into hydrocarbon fuels and chemicals and, in particular, to methods and systems for converting biomass including lignocellulosic material into pentose and hexose sugars and converting the sugars into hydrocarbon fuels and chemicals using genetically modified microorganisms.

BACKGROUND OF THE INVENTION

Global efforts are underway for the development of sustainable sources of energy, including biofuels and biochemicals, to reduce reliance on fossil fuels and reduce greenhouse gas emissions. For example, the United States, through the Energy Independence and Security Act (EISA) of 2007 and subsequently the expanded Renewable Fuel Standard (RFS) program, aims to increase the production of renewable fuel, by increasing amounts each year relative to petroleum-based fuels. Accordingly, the development of renewable or sustainable energy is of particular interest.

The use of biomass for making sustainable energy has been a focus for achieving reduced greenhouse gas emissions. The Renewable Fuel Standard targets are set to reduce emissions based on feedstock source of the biofuel. Much of the efforts to produce sustainable energy and biofuels have focused food-related biomass and conversion into light alcohols, such as ethanol. For example, ethanol has been derived from sugarcane, chemically transesterified vegetable oils, seed oils, or animal fats. A primary source of food-related biomass currently used for producing sustainable energy is derived from corn (e.g., corn starch). However, such food-related biomasses, such as corn, are major global food sources and, accordingly, these efforts for producing sustainable energy compete with food availability. Furthermore, the reduction in greenhouse gas emissions associated with biofuels developed from food-related biomass is dampened primarily due to the uncertainty associated with land use change. For example, the use of food-related biomass for fuels may require greater quantities of land (and increase deforestation) to produce both food for consumption and food-related biomass to be converted into biofuels.

As a result, new efforts, including mandates from the Renewable Fuel Standard program, have been focused on biofuels derived from non-food biomass to meet the demand for sustainable energy without competing with food resources. These non-food biomass sources include, for example, residues from agriculture, forestry, and municipal solid waste. It is estimated that sustainable energy from non-food biomass could satisfy a sizable percentage of the transportation fuel and diesel demands in the near future, thereby decreasing reliance on fossil fuels. Furthermore, the potential to reduce greenhouse gas emissions is greater because there is reduced or eliminated demand for changes in the use of land. For example, the use of biomass arising from residues from agriculture, forestry, and municipal solid waste requires little or no change in the use of land for production of food and fuels.

One source of biomass that has been of interest is non-food biomass including lignocellulose material. Lignocellulose is present in all plant biomass, and is a complex of lignin, hemicellulose, and cellulose present in plant cell walls. Such lignocellulosic material, including those derived from agricultural waste, forest residue, and energy crops, is readily available and does not compete with food resources to supply fermentable sugars that can be harnessed to produced biofuels and biochemicals.

However, lignocellulosic material can be difficult to convert to useful products. The hemicellulose and cellulose portions may be cleaved into pentose (5 carbon) and hexose (6 carbon) sugars. Pentose and hexose may undergo bioconversion to fuels or fuel precursors, for example, the sugars may be converted to fatty acids, which when esterified may be used as hydrocarbon fuels (biodiesel). The bioconversion to fuels and chemicals may be accomplished in fed-batch reactors, which are reactors in which a culture of certain microorganisms is fed and typically, in which the product remains until the end of the reactor run. The production of fatty acid esters (hydrocarbon fuels) from lignocellulosic materials remains of interest in reduction of reliance on fossil fuels and reduction of production of greenhouse gases.

There remains a need for improved methods and systems for production of biofuels.

SUMMARY OF THE INVENTION

The present disclosure relates to processes for producing hydrocarbon fuels from lignocellulosic biomass. A process may include introducing biomass to a pretreatment system forming a pretreatment effluent. The pretreatment effluent may be introduced to a first separation system forming a pentose-rich stream and a pentose-lean stream. The pentose-lean stream may be introduced to a hydrolysis system forming a hydrolysate and the hydrolysate introduced to a second separation system forming a hexose-rich stream and a lignin stream. Additionally, at least one of the pentose-rich stream or the hexose-rich stream may be introduced to a bioreactor containing microorganisms configured to produce hydrocarbon fuels.

Furthermore, the present disclosure relates to other processes for producing hydrocarbon fuels from lignocellulosic biomass. A process may include introducing biomass to a pretreatment system to form a pretreatment effluent and introducing the pretreatment effluent to a hydrolysis system to form a hydrolysate. The hydrolysate may be introduced to a sugar separation system to form a pentose-rich stream, a hexose-rich stream, and a lignin stream. At least one of the pentose-rich stream or the hexose-rich stream may be introduced to a bioreactor containing microorganisms configured to produce hydrocarbon fuels.

The present disclosure also relates to systems for the production of hydrocarbon fuels. A system may include a pretreatment system, a first separation system, a hydrolysis system, a second separation system, and one or more bioreactors.

In another embodiment, the present disclosure relates to systems for production of hydrocarbon fuels. A system may include a pretreatment system, a hydrolysis system, a sugar separation system, and one or more bioreactors.

DETAILED DESCRIPTION

Global demands motivate the development of sustainable energy sources, such as biofuels and biochemicals, which can decrease greenhouse gas emissions, decrease reliance on fossil fuels, and, ideally, do not compete with food sources. Lignocellulosic material (also referred to as lignocellulosic biomass) may be used to satisfy the global demand for sustainable energy. Furthermore, lignocellulosic biomass is readily available and may be derived from agricultural residue and waste, forest residue, and energy crops. Bioconversion processes that convert lignocellulosic biomass, especially at commercial scales, have the potential to greatly reduce greenhouse gas emissions without competing with important food resources.

The methods and systems described provide for a biological conversion of sugars obtained from lignocellulosic biomass using microorganisms, such as genetically modified *Escherichia coli* (*E. coli*), a naturally occurring microorganism found in healthy human intestines. In particular, the methods and systems described provide for conversion of sugars into fuels and chemicals, such as fatty acid methyl ester (FAME). Moreover, the methods and systems described can utilize a variety of biomass material feeds for conversion of lignocellulosic compounds, and permit production of a variety of distillate products, further enhancing commercial scalability.

In some embodiments, the present disclosure provides for a method and system that converts lignocellulosic material derived from one or more biomass sources into its primary components of hemicellulose, cellulose, and lignin. The amount of each of these primary components is specific to the type of biomass, for example, corn stover and wheat straw contain different mixtures of hemicellulose, cellulose, and lignin. The hemicellulose and cellulose are further hydrolyzed to release pentose and hexose monosaccharides. Because the amounts of hemicellulose and cellulose may be specific to a type of biomass, the ratio of pentose sugars to hexose sugars may also be specific to a particular type of biomass. The lignin is separated from the hydrolyzed material and may be burnt in a steam generator (e.g., a boiler), for example, to produce energy, such as steam and/or electricity. Additionally, unlike production of biodiesel from vegetable oil, the processes and systems using lignocellulosic feedstock do not directly compete with food production.

Furthermore, design and development of microorganisms for bioconversion of certain biomass to fuels and chemicals typically includes significant research and development costs and effort. For a particular microorganism, typically the rate of reaction of pentose and hexose sugars is different, and the overall yield an average of the yields from each sugar group. The development of a microorganism for bioconversion processes has typically been specific to a sugar type, such as hexoses, because development with a mixed sugar stream is sufficiently challenging and time consuming to make development with multiple sugars impractical. However, the bioconversion process may include a combination of sugars from a particular biomass based on the ratio of pentose and hexose sugars within that biomass. Additionally, the product yield may be negatively impacted when both pentose and hexose sugars are present because in the presence of both sugars the bioconversion process performance may be affected. One reason for the inefficiency caused by multiple types of sugar is that a batch reactor may fill (and the reaction terminate) before the microorganism has processed all the sugar in the feed source. Therefore, separating sugar feed sources allows for greater efficiency and increased production of fatty acids and their corresponding esters for use as hydrocarbon fuels and chemicals. These improved efficiencies accelerate the design and development of the microorganism and reduce time to commercial deployment.

It has further been discovered that separation of pentose and hexose monosaccharides and staggered feeding of the separated food sources to microorganisms may result in more efficient bioconversion of sugars into hydrocarbon fuels and chemicals. The separation of pentose and hexose sugars also allows for greater feedstock flexibility (e.g., various types of readily available biomass may be used, as substantially all plant matter contains lignocellulosic material) than previous processes.

Furthermore, because pentose and hexose sugars have different rates of bioconversion if a mixture of pentose and hexose sugars is fed to a bioreactor, the conversion of one class of sugars, e.g., the hexoses, can take precedent over the other one due to its higher rate of conversion. For example, the conversion of pentose sugars may be delayed until after substantially all the hexose sugars in the bioreactor are consumed because the rate of conversion of the hexose sugars can be faster than the rate of conversion of pentose sugars. In a fed-batch process delayed sugar conversion adversely impacts the process performance, reactor design, and operating conditions. Consequently, the addition of a combined sugar stream may yield poor process economics because the conversion rates of the sugar dictate the sugar and reactant feed rates and set the basis for the reactor design and geometry. Lower conversion rates can slow the sugar feed rates and creates a need for bigger reactor vessels. Additionally, the bioreactor typically is a stirred tank reactor whose maximum size is set by the practical size the impellers and the impeller motor power output. For larger processes or lower sugar conversion rates, more bioreactors may be needed adversely impacting the process economics.

However, it has been discovered that separation of the pentose and hexose sugars and feeding one group of sugars first to the bioreactor may increase the microorganism's productivity per unit volume of the bioreactor. Therefore, separating the sugar groups and controlling their feed rates to the bioreactor yields a significant improvement in the overall performance and economics of the process. Additionally, microorganism development may be improved based on consumption of a single-type of sugar over a mixture of pentose and hexose monosaccharides.

Definitions

The terms "lignocellulosic material," "lignocellulosic biomass," "lignocellulose," and grammatical variants thereof, are used interchangeably and are broad terms including a complex of namely hemicellulose, cellulose, and lignin present in the cell walls of woody plants. "Lignocellulosic feedstock," and grammatical variants thereof, includes biomass materials that include lignocellulosic material including, agricultural residues and waste (e.g., corn stover, wheat straw, bagasse), forest residues (e.g., woodchips), energy crops (e.g., switch grass, wheatgrass, bamboo), or combination(s) thereof.

The term "biomass" and grammatical variants thereof, refers to biological, organic matter that can be converted to fuel. The biomass for use in the embodiments of the present disclosure refers to plant matter.

The term "biofuel" and grammatical variants thereof, refers to a fuel derived directly or indirectly from biological, organic matter, used as an energy source (e.g., to produce heat or power).

The term "biochemical" and grammatical variants thereof, refers to a chemical product or intermediate derived directly or indirectly from a biological process.

The term "biorefinery" and grammatical variants thereof (e.g., "biorefining"), refers to a facility that integrates biomass conversion processes and equipment to produce biofuels and/or biochemicals from biomass. The equipment for use in the biorefinery systems of the present disclosure includes any suitable equipment for performing the methods described. Such equipment includes, mechanical size-reduction equipment (e.g., grinders, millers), transport conduits (e.g., hoses, pipes, conveyers, and other fluid conduits), separation equipment (e.g., decanters, centrifuges, distillation columns, molecular sieves), non-reactor tanks, seed train tanks, bioreactors, water filtration equipment, filtration equipment (e.g., belt filters, vacuum belt filter, filter press), concentration equipment (e.g., evaporators, vapor-compression evaporation equipment, molecular sieves), steam generators, heat exchangers, pumps, compressors, boilers, water purification systems (e.g., reverse osmosis, filtration, deionizers, aerobic and anaerobic digesters), storage tanks, and other equipment suitable for use in performing the methods described, or combination(s) thereof.

The terms "transesterification" and "transesterified," and grammatical variants thereof, refers to the process of exchanging an alkoxy group of an ester compound with another alcohol. Biologically, transesterification typically occurs by enzymatic exchange of an acyl-carrying protein with an alcohol.

The term "genetically modified" and grammatical variants thereof, refers to a microorganism (e.g., a bacteria) containing genetic material that has been manipulated in a laboratory through techniques of genetic engineering to produce one or more desired characteristics.

The embodiments described may include a series of concurrent, countercurrent, and single pass processes for the conversion of lignocellulosic material into biofuels and/or biochemicals.

Preparation

Raw material biomass including lignocellulosic material(s) is milled or cut into pieces at a biorefinery location to an appropriate, desired size. In some instances, such size may be about 1 centimeters (cm) to about 10 cm in length, such as about 3 cm to about 7 cm in length, regardless of the shape of the milled material. The raw material biomass may be one or more of a variety of plant matter, such as, for example, corn stover, switchgrass, wheat straw, other plant matter or combination(s) thereof. The milled biomass is transported for feed preparation. In some embodiments, the milled biomass may have a moisture content suitable for feed preparation, such as about 10% to about 40% moisture by weight of the milled biomass, such as about 20% moisture by weight of the milled biomass. Depending, for example, on the moisture content of the milled biomass, which may stem from the type of biomass and the storage conditions, the biomass may be slurried or blended (e.g., made into a thin and viscous fluid). In some embodiments, the milled biomass may be slurried in an amount of from about 0% (not slurried) to about 30% by weight of the milled biomass, such as about 20% to about 25% by weight of the milled biomass, thereby forming a prepared feed. In some embodiments, the biomass may be slurried with water. Alternatively, the now-milled biomass may be conveyed directly as a solid feed such that the milled biomass is used as the prepared feed.

Pretreatment

The conversion of lignocellulosic materials includes a pretreatment, which includes deconstruction of the prepared feed into its primary components of hemicellulose, cellulose, and lignin. Pretreatment may include: physical, physiochemical, chemical, or biological methods. Examples include, mechanical pretreatments (e.g., grinding, milling, etc.), hot water or steam (explosion) pretreatments, ammonia fibre expansion (AFEX) pretreatments, acid or alkaline pretreatments (e.g., sulfuric acid, sodium hydroxide), oxidizing agent pretreatments (e.g., hydrogen peroxide, employing ozonolysis), ionic liquids, hydrogenolysis, sulfite pulping, fungal pretreatments, enzymatic pretreatments, solvent-assisted extraction, or combination(s) thereof.

During pretreatment, hemicellulose may be broken down into sugar species including pentose and/or hexose monosaccharides, typically hemicellulose contains more pentose sugars than hexose sugars. Pentose sugars are monosaccharides including five atoms of carbon, such as xylose, rhamnose, and arabinose. Hexoses are monosaccharides including six atoms of carbon, such as glucose, galactose, and mannose. The relative amounts of pentose and hexose sugars released from hemicellulose depends on the source of lignocellulosic biomass and the employed pretreatment technologies. In some embodiments, the yield of pentose monosaccharides from dry biomass feed may be about 10% to about 30%, such as about 20% to about 25% by weight of the biomass. The pretreatment technologies can be selected based on the treatment's ability to release each sugar component. Pretreatment produces a pretreatment effluent that may include aqueous solution of monosaccharides, cellulose, lignin, and/or a portion of the hemicellulose including oligosaccharides that were not broken down during pretreatment.

In some embodiments, condensed water is removed from the pretreatment system and may contain about 1 to 2 wt % organic impurities. The condensed water may be sent to an anaerobic and/or aerobic digester for treatment. The treated water therefrom may thereafter be reused and/or filtered for other uses. In some embodiments, the condensed water that has been treated and/or filtered may be reused within the biological conversion processes. Further, in some instances, the anaerobic digester may be used to produce and harness biogas (including mostly methane) and an organic-rich, high-solid content (sludge).

Other by-products may additionally be released during hemicellulose pretreatment such as, for example, organic acids (e.g., formic acid, acetic acid, carboxylic acid, furoic acid), furans (e.g., furfurals, hydroxymethylfurfuals), and combinations thereof. Hemicellulose pretreatment may be achieved by any of the suitable methods described above, and in some embodiments, is achieved using an acid pretreatment (e.g., by employing a mild acid reaction using, for example, a dilute sulfuric acid solution). The acid pretreatment may be performed with loadings of about 5 milligrams (mg) of acid per gram (g) of biomass to about 30 mg of acid per g of biomass, such as about 10 mg, about 15 mg, about 20 mg, about 25 mg, or about 30 mg of acid per g of biomass, or from about 5 mg to about 30 mg, from about 10 mg to about 20 mg, or from about 10 mg to about 15 mg of acid per gram of biomass. The concentration of pentose and hexose, as well as the type and concentration of by-products may depend on a number of factors including, the type of biomass being pretreated, the pretreatment method selected, the conditions related to the pretreatment method, and combinations of these or other factors.

First Separation System

The pretreatment effluent may be sent to a separation system for separation of a pentose-rich stream and a pentose-lean stream. The separation may include any suitable method of separation of the aqueous pentose solution from the remaining solids, such as physical physio-chemical, chemical, or biological methods. Examples may include: filtering, pressing, membranes, centrifugation, or combination(s) thereof.

Hydrolysis System

The pentose-lean stream may include lignin, cellulose, and hemicellulose that was not broken down during pretreatment. The pentose-lean stream may be further hydrolyzed to release remaining sugars as monosaccharides, which may be accomplished by any suitable method, including methods described for pretreatment, and, in some embodiments, may be achieved using enzymatic hydrolysis. Enzymatic hydrolysis may be performed in the presence of enzymes derived from various organisms, including Bacteria, Archaea, or Fungi. The enzymes may be purchased commercially and/or manufactured directly at a biorefining site (at a location that the biological conversion of biomass containing lignocellulosic materials is performed).

In some embodiments, the enzyme used for the hydrolysis portion is prepared on-site at the biorefinery location and is fed to the hydrolysis system for performance of the hydrolysis portion of the methods and systems described. One or more feeds may provide various nutrients (e.g., sugars, vitamins, and salts) to support the production of the enzyme. Alternatively or additionally, the enzymes may be produced at another location or otherwise outside of the flow of the biological conversion process and thereafter fed into the hydrolysis system, such as in fermentation equipment, appropriate laboratory, or purchased commercially, without departing from the scope of the present disclosure.

Examples of suitable enzymes may include, one or more cellulases and/or hemicellulases that aid in the decomposition of cellulose. Such cellulases may include an endoglucanase, an exoglucanase, a β-glucosidase, or combination(s) thereof. Enzyme loadings can vary depending on the enzyme mix, but may be from about 5 mg of enzyme per g of cellulose to about 25 mg of enzyme per g of cellulose, such as about 5 mg, about 10 mg, about 15 mg, about 20 mg, or about 25 mg, of enzyme per g of cellulose, or from about 5 mg to about 25 mg, from about 10 mg to about 20 mg, or from about 10 mg to about 15 mg of enzyme per g of cellulose. Hydrolysis may convert at least a portion of the cellulose and remaining hemicellulose to hexose monosaccharides, such as glucose, and may also yield additional pentose monosaccharides (e.g., in addition to those obtained from the breakdown of the hemicellulose). A typical yield of hexose monosaccharides from dry biomass feed may be about 25% to about 45% by weight, such as about 30% to about 40% by weight. Typically the pentose-lean stream contains few pentose sugars, for example the pentose-lean stream may contain about 30 wt % or less, 25 wt % or less, 20 wt % or less, 15 wt % or less, 10 wt % or less, or 5 wt % or less of pentose sugars. Hydrolysis produces a hydrolysate that may include aqueous solution of monosaccharides, lignin and/or a portion of the cellulose or hemicellulose that was not broken down during hydrolysis.

While the byproducts are released during pre-treatment, other by-products may additionally be released during hydrolysis of the pentose-lean stream such as, for example, organic acids (e.g., formic acid, acetic acid, carboxylic acid, furoic acid), furans (e.g., furfurals, hydroxymethylfurfuals), and combinations thereof.

Second Separation System

The hydrolysate may be sent to a second separation system for separation of a hexose-rich stream and a lignin stream including the remaining solids, which are mostly lignin, but may include portions of cellulose or hemicellulose that were not broken down during hydrolysis. The separation may include any suitable method of separating the aqueous hexose-rich stream from the lignin stream, such as depolymerization, filtration, membranes, centrifugation, or combination(s) thereof. In some embodiments, the insoluble lignin in the aqueous hydrolysate is removed by filtration (e.g., vacuum filtration, belt filtration, press filters). The filtration process removes all or substantially all lignin and insoluble solids in the hydrolysate producing the lignin stream, while retaining about 80 wt % or greater, such as about 90 wt % or greater, about 95 wt % or greater, about 98 wt % or greater, or about 99 wt % or greater of the sugars in the liquid phase hexose-rich stream that is substantially lignin-free, based on the total weight of sugars in the hexose-rich stream. During filtration processes, water may be injected to facilitate filtration and removal of lignin and other insoluble solids. Water may be obtained from the anaerobic/aerobic digestion process of waste water and subsequent water filtration of other processes.

The lignin stream may include a moisture content, such as about 20 wt % to about 40 wt % moisture content, and can be transported to a boiler/steam generator. The steam generator may, for example, be used to generate heat to produce high pressure, superheated steam. The steam created by the steam generator may be used to satisfy the steam demands of the biological conversion processes, such as, for example, enzyme production, ion exchange bed regeneration (e.g., the purification system), sterilization needs (e.g., sterilization of bioreactors including seed trains and aerobic fermentation), one or more pentose separation units, one or more hexose separation units, or combination(s) thereof. Excess high pressure superheated steam may be sent to a turbo expander (or expansion turbine) equipped, for example, with an electrical generator to produce electricity which may thereafter be used to supply the electrical demands of the biological conversion processes. Excess power is exported to support other electrical needs within the biorefinery and/or outside of the biorefinery, as appropriate. In another embodiment, the moisture content in the lignin stream can be lowered by drying and the lignin repurposed. For example, the dried lignin may be sold as a source of revenue or used as process fuel in the bioconversion systems and processes. Thus, the biological conversion platform may recycle resources to provide integrated fuel, steam, and electrical needs.

Sugar Separation System

In some cases the pretreatment effluent is sent directly to the hydrolysis system and the hydrolysate may be sent to a sugar separation system for separating solids from the mixed sugar solution and additional separation of pentose and hexose sugars. The separation of the solids produces a lignin-free stream including both hexose and pentose sugars, and a lignin stream including the remaining solids, which are mostly lignin, but may include portions of cellulose or hemicellulose that were not broken down during hydrolysis. The solid separation may include any suitable method of separating the aqueous lignin-free stream from the lignin stream, such as depolymerization, filtration, centrifugation, or combination(s) thereof. In some embodiments, the insoluble lignin in the aqueous hydrolysate is removed by filtration (e.g., vacuum filtration, belt filtration). The filtration process removes all or substantially all lignin and insoluble solids in the hydrolysate producing the lignin stream, while retaining about 80 wt % or greater, such as about 90 wt % or greater, about 95 wt % or greater, about 98 wt % or greater, or about 99% or greater of the sugars in the liquid phase lignin-free stream that is substantially lignin-free, based on the total weight of sugars in the lignin-free stream. During filtration processes, water may be injected to facilitate filtration and removal of lignin and other insoluble solids. Water may be obtained from the anaerobic/aerobic digestion process of waste water and subsequent water filtration of other processes.

The following separation separates the lignin-free stream into a pentose-rich stream and a hexose-rich stream. The separation of the sugars may include any suitable method of separating pentose sugars from hexose sugars, such as adsorption, chromatography, simulated moving bed, or selective membranes. In some embodiments, the pentose sugars are adsorbed in a zeolite and the hexose sugars remain in the aqueous solution forming a hexose-rich stream and the pentoses are desorbed from the zeolite forming a pentose-rich stream.

Concentration

The now lignin-free or substantially lignin-free pentose-rich stream and hexose-rich stream typically have a relatively low concentration of monosaccharides, such as from about 5% to about 20%, or about 10% to about 15%, by weight of the lignin-free stream. A "lignin-free stream" is any of the pentose-rich stream, the hexose-rich stream, or a combination thereof.

In some embodiments, a lignin-free stream may be concentrated to facilitate production of biofuel and/or biochemicals, such as to reduce equipment size (e.g., smaller bioreactors) and facilitate processing. Concentration may be achieved by any suitable methods including, vapor compression evaporation (e.g., mechanical vapor compression or thermocompression), membrane filtration (e.g., ultrafiltration membranes), reverse osmosis, or combination(s) thereof. Concentration of a lignin-free stream yields a sugar content of the concentrated effluent of about 30% to about 60% by weight of the concentrated effluent (product of concentration of a lignin-free stream), such as about 40% to about 50% by weight of the concentrated effluent.

Excess water may be removed during concentration and be sent to anaerobic and/or aerobic digestion for further processing and reuse in the biological conversion processes.

Purification

After pretreatment and/or hydrolysis, a lignin-free stream may include a wide variety of compounds, such as water, monosaccharides, and various produced by-products. Some by-products may be harmful or toxic to the microorganism (e.g., a genetically modified E. coli) used in conversion of monosaccharides into biofuel or biochemical products. Additionally, some by-products may not be directly harmful or toxic to the microorganism, but may inhibit the bioconversion processes.

Furthermore, during the concentration step of a lignin-free stream, other harmful by-products (e.g., the toxins/inhibitors described above) may also be concentrated, which can effectively render the microorganism used later in the biological conversion process ineffective.

Accordingly, a lignin-free stream may be purified prior to being used as a feed in bioconversion processes. The purification may remove by-products and other undesirable impurities. Purification may be achieved by any suitable methods including physical, chemical, or biochemical purification procedures, such as the use of chemical reducing agents, adsorption beds (e.g., ion exchange resin beds, activated carbon beds), liquid-liquid extraction, reactive extraction, evaporation, bio-conversion (e.g., use of enzymes or using microorganism strains, including genetically modified microorganism strains), or combination(s) thereof Bioconversion to Fuels and/or Chemicals A concentrated and/or purified lignin-free stream may be fed into an aerobic bioreactor including a genetically modified bacteria, such as E. coli, that is initially grown (e.g., replicated in a series of batch reactors of a seed train) and used to metabolically convert the sugars into fatty acid. The combined lignin-free stream and genetically modified bacteria stream is introduced into the bioreactor at an initial volume of about 10% to about 40% by volume of the bioreactor, such as about 20% to about 30% by volume of the bioreactor. The amount of a lignin-free stream that is added is determined by the desired sugar concentration of the microorganism used. The lignin-free stream may provide nutrients to continue the growth (replication) of the microorganisms.

The microorganism population in the bioreactor is monitored until the population concentration reaches a desired or a suitable level; generally, at the suitable concentration, the microorganisms begin producing fatty acid. Upon reaching the desired level, additional sugars are introduced into the bioreactor to facilitate further production of fatty acid in the cells of the genetically modified microorganisms. The fermentation and biological conversion process of the embodiments described may be aerobic, with the microorganisms producing fatty acids within their cells and in the process releasing carbon dioxide ($CO_2$). Oxygen or air is pumped into the bioreactor to maintain aerobic respiration in the bioreactor, and in some embodiments, is sparged into the production bioreactor, such as from the bottom thereof. The $CO_2$ may be vented at a given concentration, such as at a concentration of about 10% to 30%, such as 15% to 25%, 18% to 22%, or 19% to 20% and the balance is air used in the aerobic process.

The microorganism population may be monitored to determine feed rates of a lignin-free stream including either pentose or hexose sugars. For example, a pentose-rich lignin-free stream may be fed to a first bioreactor including a microorganism and a hexose-rich lignin free stream may be fed to a second bioreactor including the same microorganism. The growth in microorganism population of the first reactor and the second reactor provide flow rates for the different sugar types. This may allow for both pentose and hexose sugars to be fed to a bioreactor at a rate where consumption of both sugars is improved.

Any suitable genetically modified microorganism or microorganisms may be used in accordance with the methods and systems described. In some embodiments, a microorganism is genetically modified using current, available molecular biology tools to enhance the microorganism's metabolism and physiology to improve the conversion of biomass monosaccharides into fatty acids, such as fatty acid esters (e.g., FAME or FAEE). A microorganism may be genetically modified to improve the conversion of a single sugar type (e.g. pentoses) to fatty acid esters. An example of a suitable genetically modified microorganism for use in the embodiments described is genetically modified *E. coli* disclosed in U.S. Patent Publication No. 2017/0175152, incorporated by reference. Fatty acid-derived biofuels and biochemicals are viable, renewable, sustainable, and cost-effective alternatives to traditional fossil fuels. The pathway for fatty acid biosynthesis in bacteria, such as *E. coli*, generally is carried out by a fatty acid synthase (FAS) enzyme. FAS is a multi-enzyme protein that catalyzes fatty acid synthesis in the presence of an alcohol by one or more biological pathways, which can be harnessed to produce biofuels and/or biochemicals.

The development and genetic modification of microorganisms may be simplified by using a single sugar type as a feed source, because, instead of attempting to modify a microorganism to have a high rate of conversion for multiple feedstocks, the process can be accomplished with a single feedstock. Furthermore, developing a microorganism on a single feedstock may enhance preference for that sugar-type.

A bioconversion reactor may include one or more microorganisms. For example, a microorganism with high conversion of pentose sugars may be introduced with pentose sugars initially, and, as the pentose sugars are converted, the bioreactor may accept an additional microorganism capable of higher hexose conversion than the first microorganism. Alternatively, a bioreactor may have one microorganism suitable for conversion of both pentose and hexose sugars and may receive one or both types of sugars. Furthermore, a bioreactor may only receive one type of sugar (e.g. pentose sugars) depending on the productivity of the microorganism or microorganisms within that reactor.

The fatty acid is thereafter transesterified using one or more alcohols including methanol, ethanol, or combination(s) thereof. For example, the fatty acid may be transesterified using methanol to produce a fatty acid methyl ester (FAME) or ethanol to produce a fatty acid ethyl ester (FAEE). Methanol may be obtained commercially and introduced into the bioreactor. Ethanol may also be obtained commercially. Alternatively or additionally, methanol or ethanol may be produced in situ in the bioreactor through fermentation of sugar(s) in the bioreactor. In some embodiments, a combination of alcohols (e.g., a combination of methanol and ethanol) may be used in the bioreactor, resulting in a combination of fermented fatty acids. Typically, the concentration of alcohol included in the bioreactor may about 1 wt % to about 10 wt % based on the total weight of the sugar concentrated effluent described (e.g., a lignin-free stream fed to the reactor), such as about 3% to about 7% by weight of the sugar concentrated effluent. The alcohol may be injected into the one or more bioreactors by any suitable means, such as one or more injection points at the bottom thereof, the top thereof, other points along the axis of the bioreactor, or combination(s) thereof.

The systems and methods described may include one or more bioreactors. Such bioreactors may operate in batch, fed-batch, or continuous mode. The one or more bioreactors may be any suitable bioreactors including those using sparged stirred-tank reactors, bubble column reactors, or combination(s) thereof. Heat generated during the fermentation within a bioreactor may be removed by any suitable methods including, use of internal cooling lines, jacketed walls, loop around (external) cooling lines, and external refrigeration. In some embodiments of the present disclosure, the one or more bioreactors include internal cooling lines in combination with stirred tanks that are designed as a coil around the mixing impeller shaft to act as a draft tube to enhance liquid circulation and cooling. Moreover, one or more impellers of different types may be employed in the one or more bioreactors, such as axial impeller(s) or radial impeller(s). In some embodiments, greater than one and/or greater than one type of impeller may be used in the bioreactors described. In some embodiments, the one or more bioreactors may include a bubble column with internal cooling lines.

Product Recovery

When a batch reactor fills to substantial or complete capacity the feed is stopped and the products recovered. The effluent from the bioreactor is sent to a recovery block where the organic hydrocarbon is removed from the aqueous stream using a series of decanter vessels and further purified, such as to a purification level of 99% by weight (wt %) or higher (e.g., about 99.5 wt %), with the balance being aqueous phase with impurities. Such purification may be achieved by any suitable methods including centrifugation, water washing, membranes, or combination(s) thereof. The now substantially empty bioreactors can be sterilized, typically with steam at high pressure, and then put back on stream. Consequently, there are reactors with different fill levels as a function of time on stream.

Various waste waters are obtained throughout the biological conversion process, including from the pretreatment, hydrolysis, concentration, product recovery, or other process(es). These waste waters can be reprocessed, such as by using an anaerobic and/or aerobic digester to remove organic impurities, including further coupling with water filtration methods. For example, the aqueous phase effluent from product recovery may be transported to an anaerobic and/or aerobic digester for further processing and reuse in the biological conversion processes. The anaerobic and/or aerobic digesters may be configured in the biological conversion processes to receive one or more of the waste waters (e.g., pretreatment water, condensation water, aqueous phases) generated during the process. Digested water may be further filtered and reused in the biological conversion processes, such as to the filter press for lignin separation, the feed preparation, and/or steam generation for other process(es). Various filtration methods may be used, such as ultrafiltration, nanofiltration, reverse osmosis, or combination(s) thereof. Through digestion and reuse of waste waters, as well as in other ways, the biological conversion systems and methods facilitate an integrated process that recycles certain elements for conservation of power and resources. In some embodiments, additional fresh water may also be introduced into the biological conversion processes of the present disclosure, as needed. In other embodiments, additional fresh water and/or recycled water may be introduced into the system to facilitate enzyme production, enzymatic hydrolysis, product recovery, or utility needs.

Biogas (e.g., gaseous fuel, methane, fermentation products) and sludge, an organic-rich slurry, generated in an anaerobic digester may be burned in a boiler to generate steam for turbines to produce power, which can be utilized in the biological conversion processes or in other processes requiring power. Further contributing to the integrated nature of the biological conversion systems and processes described. Also, an aerobic digester may be used to further decompose remaining organic species carried over from the anaerobic digester. Accordingly, the biological conversion processes of the present disclosure allow for heat, power, and steam integration.

Figure 1:
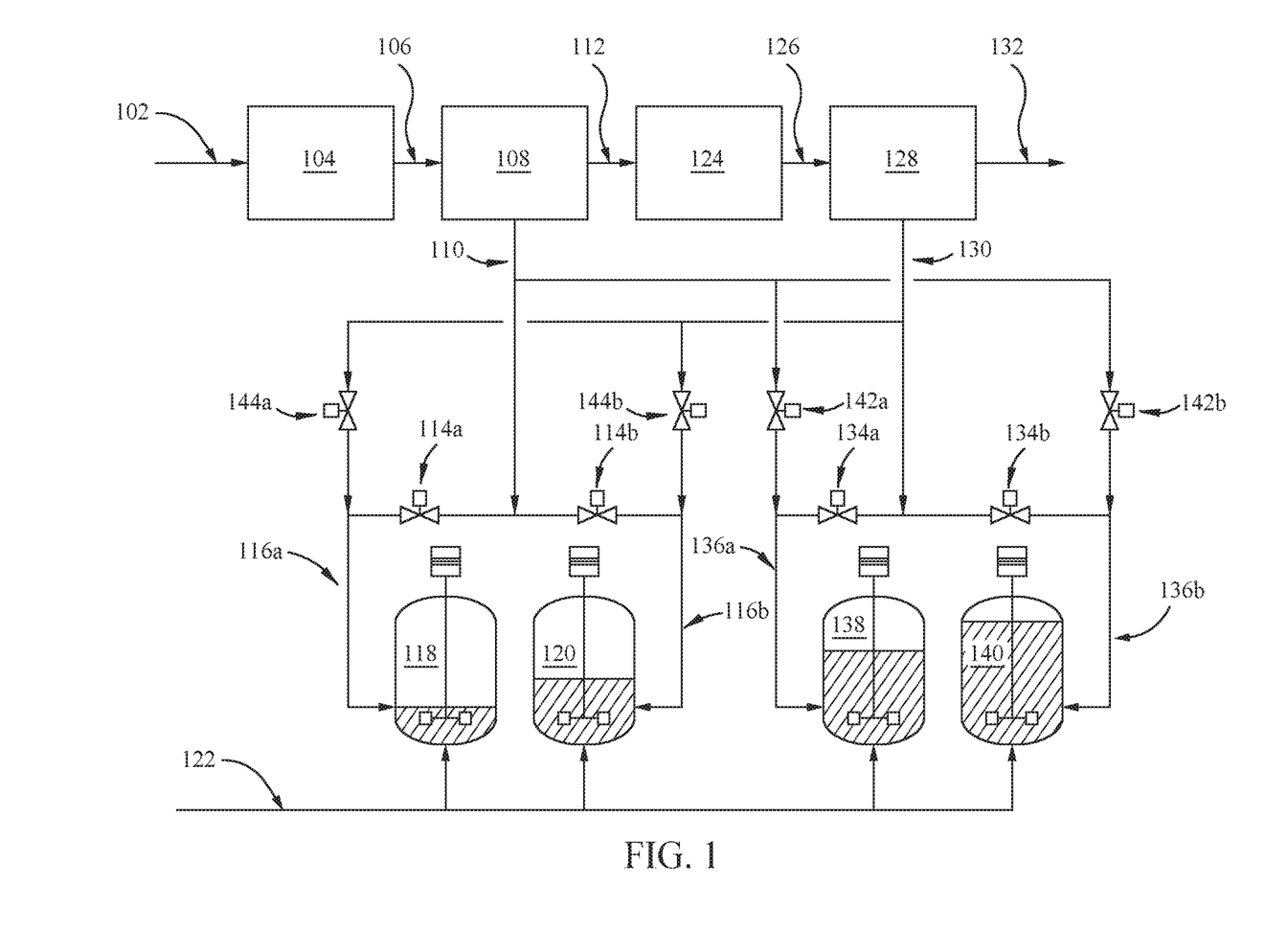
FIG. 1 depicts a schematic of a system for bioconversion of lignocellulosic biomass to hydrocarbon fuel and/or chemicals according to an embodiment.

Referring now to FIG. 1, FIG. 1 is a schematic of a system for bioconversion of sugars obtained from lignocellulosic biomass to hydrocarbon fuel and/or chemicals. The prepared feed 102 is introduced to pretreatment system 104, a deconstruction portion of the biological conversion system. In pretreatment system 104, the prepared feed 102 is deconstructed or broken down into its main constituent parts (hemicellulose, cellulose, and lignin) using one or more pretreatment methods, such as an acid pretreatment coupled with a steam (explosion) pretreatment.

The pretreatment effluent 106 including hemicellulose, cellulose, lignin, and released pentose sugars is thereafter separated in first separation system 108 into a pentose-rich stream 110 and a lignocellulosic pentose-lean stream 112. In some embodiments, first separation system 108 includes the ability to concentrate the sugars in pentose-rich stream 110. In some embodiments, first separation system 108 includes purification of pentose-rich stream 110 to remove impurities that may be toxic to or inhibit the bioconversion processes. The pentose-rich stream may be sent via valve 114a and line 116a to bioreactor 118. Additionally or alternatively, the pentose-rich stream may be sent via valve 114b and line 116b to bioreactor 120. Bioreactors 118 and 120 are configured to receive additional reactants such as air and alcohol via sparge line 122.

The pentose-lean stream 112 may be sent to hydrolysis system 124 to produce a hydrolysate. The hydrolysate may include hexose and pentose monosaccharides, and solid matter including lignin, cellulosic materials that were not broken down in the hydrolysis system such as cellulose, hemicellulose, disaccharides, and oligosaccharides resistant to hydrolysis methods employed. The hydrolysate may be sent through line 126 to second separation system 128 where solid material is separated from aqueous sugars producing a hexose-rich stream 130 and a lignin stream removed via line 132. In some embodiments, second separation system 128 includes the ability to concentrate the sugars in hexose-rich stream 130. In some embodiments, second separation system 128 includes purification of hexose-rich stream 130 to remove impurities that may be toxic to or inhibit the bioconversion processes. The hexose-rich stream may be sent via valve 134a and line 136a to bioreactors 138. Additionally or alternatively, the hexose-rich stream may be sent via valve 134b and line 136b to bioreactor 140. Bioreactors 138 and 140 are configured to receive additional reactants such as air and alcohol via sparge line 122.

Additionally, pentose-rich stream 110 may connect to bioreactors 138 and 140 via lines 136a and/or 136b through valves 142a and 142b allowing for pentose-rich stream 110 to be directed to one or more of the bioreactors. Furthermore, hexose-rich stream 130 may connect to bioreactors 118 and 120 via lines 116a and 116 b through valves 144a and 144b allowing for hexose-rich stream 130 to be directed to one or more of the bioreactors.

In some embodiments, reactors 118 and 120 contain microorganism(s) that has been engineered for efficiency in bioconversion of a sugar, such as pentose sugars. In some embodiments, reactors 138 and 140 contain microorganism(s) that has been engineered for efficiency in bioconversion of a sugar, such as hexose sugars. In other embodiments reactors 118, 120, 138, and 140 contain the same microorganism(s) and are fed the pentose-rich stream and the hexose-rich stream at different times on stream.

Bioreactors 118, 120, 138, and 140 are shown at different fill levels as a function of different times on stream. As aqueous sugars are added to a fed-batch reactor the microorganisms multiply and the combination of microorganism growth and additional materials fill the bioreactor. Initially, a quantity of microorganism can be introduced to bioreactors 118, 120, 138, and 140 from a seed train, which may include another series of bioreactors designed to aid in the growth and replication of the microorganism. Typically the microorganism(s) and a lignin-free stream are introduced to a bioreactor at an initial volume of about 10% to about 40% by volume of the bioreactor, or about 20% to about 30% by volume of the bioreactor. The bioreactor then receives additional lignin-free stream, including sugars (whether pentose or hexose monosaccharides) and as the time on stream increases the volume of material within the reactor increases until the reactor is full. Once the reactor is full, the material is removed and the product(s) are recovered.

In some embodiments, the pentose-rich stream and the hexose-rich stream are fed to the bioreactors at different rates based on the microorganism's ability to process the different sugars. For example, the pentose-rich stream may be fed at a rapid initial rate that declines with time on stream (or bioreactor fill level), while the hexose-rich stream is fed at a low initial rate that increases as a function of time on stream (or bioreactor fill level). Additionally, the flow rates of the same sugar type could vary from one reactor to another, e.g., the flow rate of hexose-rich stream to reactor 138 could be greater than, equal to, or less than the flow rate of hexose-rich stream to reactor 140 based on the performance of the microorganism as a function of sugar concentration in the bioreactor.

In some embodiments, the pentose-rich stream and the hexose-rich stream are fed to the bioreactors at different time on stream (TOS) allowing the microorganism to process a sugar type, such as pentoses, and then another sugar type, such as hexoses (or vice versa). In such embodiments, the microorganism need not finish processing one sugar type or the addition of the first sugar type be stopped before additional sugar types are added, such that there may be more than one sugar type in the bioreactor.

Depending on microorganism performance, it may be desirable to switch feed type during a reactor run. For example, reactors 118 and 120 may initially receive a pentose-rich stream via line 110, and before the reactor reaches capacity could be switched to a hexose-rich stream. The change in feeds may be accomplished by closing valves 114a and/or 114b and opening valves 144a and/or 144b. The change in feeds may be dependent on the time on stream of a bioreactor. Furthermore, with different reactors at different times on stream it may be advantageous to allow for stopping a feed. For example, when bioreactors 138 and/or 140 reach the end of the batch process, the hexose-rich stream may be stopped by closing valves 134a and/or 134b, the reactors may be purged and prepared to receive a pentose-rich stream via the opening of valves 142a and/or 142b. In some embodiments, the feed is switched from a pentose-rich stream to a hexose-rich stream before the end of a batch. In other embodiments, the feed is switched from a hexose-rich stream to a pentose-rich stream before the end of a batch. Alternatively, a microorganism may be developed that sufficiently prefers one sugar stream such that a bioreactor might only receive one feed, e.g. only a pentose-rich stream.

Figure 2:
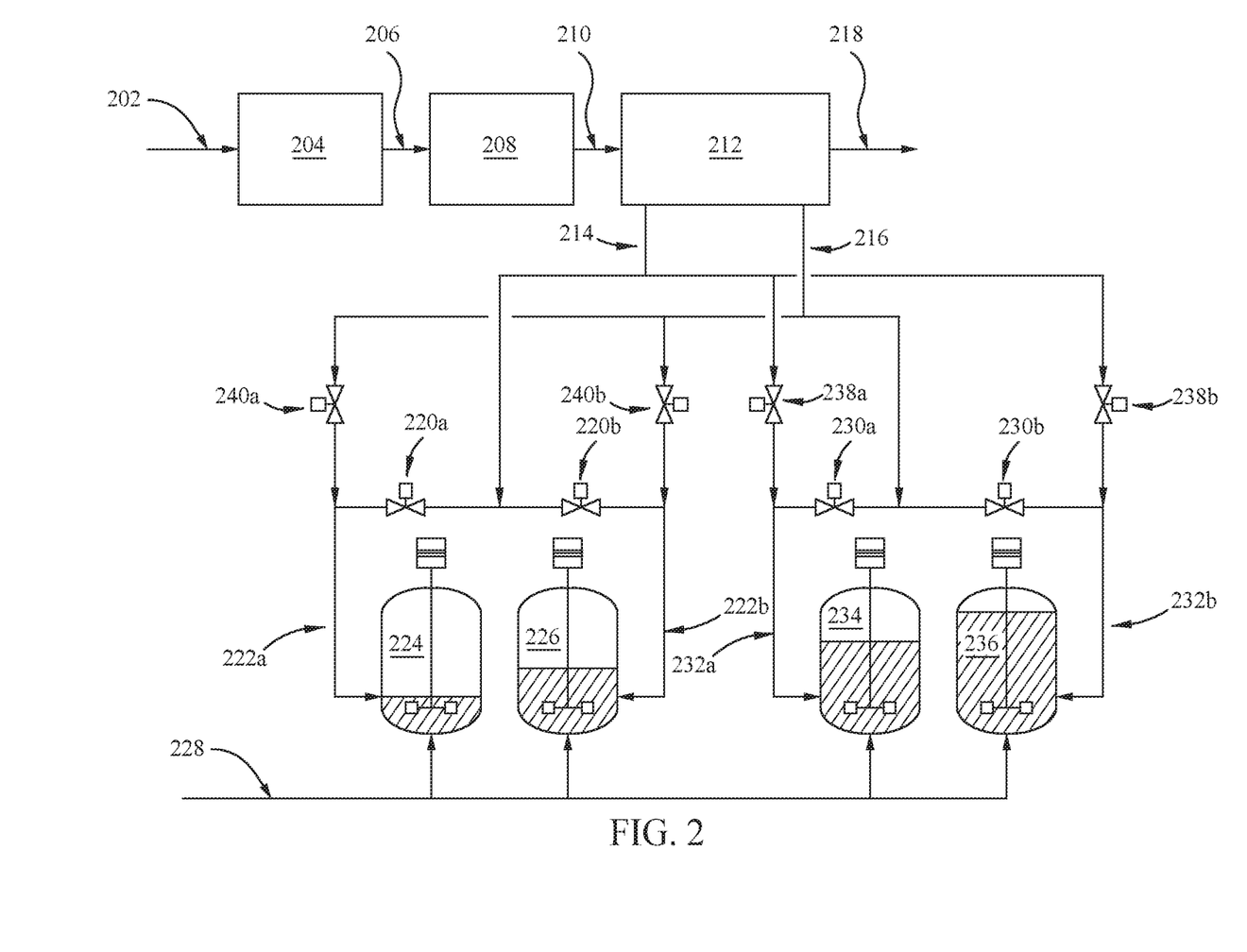
FIG. 2 depicts a schematic of a system for bioconversion of lignocellulosic biomass to hydrocarbon fuel and/or chemicals according to an embodiment.

Referring to FIG. 2 a schematic of a system for bioconversion of sugars obtained from lignocellulosic biomass to hydrocarbon fuels and/or chemicals. The prepared feed 202 is introduced to pretreatment system 204, a deconstruction portion of the biological conversion system. In pretreatment system 204, the prepared feed 202 is deconstructed or broken down into its main constituent parts (hemicellulose, cellulose, and lignin) using one or more pretreatment methods, such as an acid pretreatment coupled with a steam (explosion) pretreatment.

The pretreatment effluent 206 including hemicellulose, cellulose, lignin, and released sugars is sent to hydrolysis system 208 to produce a hydrolysate. The hydrolysate may include hexose and pentose monosaccharides, and solid matter including lignin, cellulosic materials that were not broken down in the hydrolysis system such as cellulose, hemicellulose, and oligosaccharides resistant to hydrolysis methods employed. The hydrolysate may be sent through line 210 to sugar separation system 212 where solid material is separated from aqueous sugars and the sugar types are separated producing a pentose-rich stream 214, a hexose-rich stream 216, and a lignin stream removed via line 218. In some embodiments, sugar separation system 212 includes the ability to concentrate the sugars in either or both of the pentose-rich stream 214 or the hexose-rich stream 216. In some embodiments, sugar separation system 212 includes purification of either or both of the pentose-rich stream 214 or the hexose-rich stream 216 to remove impurities that may be toxic to or inhibit the bioconversion processes.

The pentose-rich stream may be sent via valve 220a and line 222a to bioreactor 224. Additionally or alternatively, the pentose-rich stream may be sent via valve 220b and line 222b to bioreactor 226. Bioreactors 224 and 226 are configured to receive additional reactants such as air and alcohol via sparge line 228. The hexose-rich stream may be sent via valve 230a and line 232a to bioreactor 234. Additionally or alternatively, the hexose-rich stream may be sent via valve 230b and line 232b to bioreactor 236. Bioreactors 234 and 236 are configured to receive additional reactants such as air and alcohol via sparge line 228.

Additionally, pentose-rich stream 214 may connect to bioreactors 234 and 236 via lines 232a and 232b through valves 238a and 238b allowing for pentose-rich stream 214 to be directed to one or more of the bioreactors. Furthermore, hexose-rich stream 216 may connect to bioreactors 224 and 226 via lines 222a and 22b through valves 240a and 240b allowing for hexose-rich stream 216 to be directed to one or more of the bioreactors.

In some embodiments, reactors 224 and 226 contain microorganism(s) that has been engineered for efficiency in bioconversion of a sugar, such as pentose sugars. In some embodiments, reactors 234 and 236 contain microorganism(s) that has been engineered for efficiency in bioconversion of a sugar, such as hexose sugars. In other embodiments reactors 224, 226, 234, and 236 contain the same microorganism(s) and are fed the pentose-rich stream and the hexose-rich stream at different times on stream.

In some embodiments, the pentose-rich stream and the hexose-rich stream are fed to the bioreactors at different rates based on the microorganism's ability to process the different sugars. For example, the pentose-rich stream may be fed at a rapid initial rate that declines with time on stream (or bioreactor fill level), while the hexose-rich stream is fed at a low initial rate that increases as a function of time on stream (or bioreactor fill level). Additionally, the flow rates of the same sugar type could vary from one reactor to another, e.g., the flow rate of hexose-rich stream to reactor 234 could be greater, equal, or less than the flow rate of hexose-rich stream to reactor 236 based on the performance of the microorganism as a function of sugar concentration in the bioreactor.

In some embodiments, the pentose-rich stream and the hexose-rich stream are fed to the bioreactors at different times on stream allowing the microorganism to process a sugar type, such as pentoses, and then another sugar type, such as hexoses. In such embodiments, the microorganism need not finish processing one sugar type or the addition of the first sugar type be stopped before additional sugar types are added, such that there may be more than one sugar type in the bioreactor. Similarly to the description of FIG. 1 and depending on microorganism performance it may be desirable to switch feed type during a reactor run. In some embodiments, the feed is switched from a pentose-rich stream to a hexose-rich stream before the end of a batch.

In other embodiments, the feed is switched from a hexose-rich stream to a pentose-rich stream before the end of a batch. Alternatively, a microorganism may be developed that sufficiently prefers one sugar stream that a bioreactor may only receive one feed, e.g. only a pentose-rich stream.

Embodiments

Clause 1. A process for producing hydrocarbon fuels from lignocellulosic biomass, the process comprising:
  introducing biomass to a pretreatment system forming a pretreatment effluent;
  introducing the pretreatment effluent to a first separation system forming a pentose-rich stream and a pentose-lean stream;
  introducing the pentose-lean stream to a hydrolysis system forming a hydrolysate;
  introducing the hydrolysate to a second separation system forming a hexose-rich stream and a lignin stream; and
  introducing at least one of the pentose-rich stream or the hexose-rich stream to a bioreactor containing microorganisms configured to produce hydrocarbon fuels.

Clause 2. The process of clause 1, further comprising concentrating the pentose-rich stream to a sugar concentration of 40 wt % to 60 wt %.

Clause 3. The process of any of clauses 1 to 2, further comprising concentrating the hexose-rich stream to a sugar concentration of 40 wt % to 60 wt %.

Clause 4. The process of any of clauses 1 to 3, further comprising purifying the pentose-rich stream.

Clause 5. The process of any of clauses 1 to 4, further comprising purifying the hexose-rich stream.

Clause 6. The process of any of clauses 1 to 5, further comprising recovering at least one of fatty acid methyl ester or fatty acid ethyl ester from the bioreactor.

Clause 7. The process of any of clauses 1 to 6, wherein introducing the at least one of the pentose-rich stream or the hexose-rich stream to a bioreactor further comprises introducing the pentose-rich stream to the bioreactor before introducing the hexose-rich stream to the bioreactor.

Clause 8. The process of any of clauses 1 to 6, wherein introducing the at least one pentose-rich-stream or the hexose-rich stream to a bioreactor further comprises introducing the pentose-rich stream to the bioreactor at an initial rate higher than an initial rate of introducing the hexose-rich stream to the bioreactor.

Clause 9. The process of any of clauses 1 to 6, wherein introducing the at least one of the pentose-rich stream or the hexose-rich stream to a bioreactor comprises introducing the pentose-rich stream at a rate that declines with time on stream.

Clause 10. The process of any of clauses 1 to 6, wherein introducing the at least one of the pentose-rich stream or the hexose-rich stream to a bioreactor comprises introducing the hexose-rich stream at a rate that increases with time on stream.

Clause 11. The process of any of clauses 1 to 6, wherein introducing the at least one of the pentose-rich stream or the hexose-rich stream to a bioreactor comprises introducing the pentose-rich stream to the bioreactor and introducing the hexose-rich stream to a second bioreactor.

Clause 12. A process for producing hydrocarbon fuels from lignocellulosic biomass, the process comprising:
 introducing biomass to a pretreatment system to form a pretreatment effluent;
 introducing the pretreatment effluent to a hydrolysis system to form a hydrolysate;
 introducing the hydrolysate to a sugar separation system to form a pentose-rich stream, a hexose-rich stream, and a lignin stream; and
 introducing at least one of the pentose-rich stream or the hexose-rich stream to a bioreactor containing microorganisms configured to produce hydrocarbon fuels.

Clause 13. The process of clause 12, further comprising concentrating the pentose-rich stream to a sugar concentration of 40 wt % to 60 wt %.

Clause 14. The process of any of clauses 12 to 13, further comprising concentrating the hexose-rich stream to a sugar concentration of 40 wt % to 60 wt %.

Clause 15. The process of any of clauses 12 to 14, further comprising purifying the pentose-rich stream.

Clause 16. The process of any of clauses 12 to 15, further comprising purifying the hexose-rich stream.

Clause 17. The process of any of clauses 12 to 16, further comprising recovering at least one of fatty acid methyl ester or fatty acid ethyl ester from the bioreactor.

Clause 18. The process of any of clauses 12 to 17, wherein introducing the at least one of the pentose-rich stream or the hexose-rich stream to a bioreactor further comprises introducing the pentose-rich stream to the bioreactor before introducing the hexose-rich stream to the bioreactor.

Clause 19. The process of any of clauses 12 to 17, wherein introducing the at least one pentose-rich-stream or the hexose-rich stream to a bioreactor further comprises introducing the pentose-rich stream to the bioreactor at an initial rate higher than an initial rate of introducing the hexose-rich stream to the bioreactor.

Clause 20. The process of any of clauses 12 to 17, wherein introducing the at least one of the pentose-rich stream or the hexose-rich stream to a bioreactor comprises introducing the pentose-rich stream at a rate that declines with time on stream.

Clause 21. The process of any of clauses 12 to 17, wherein introducing the at least one of the pentose-rich stream or the hexose-rich stream to a bioreactor comprises introducing the hexose-rich stream at a rate that increases with time on stream.

Clause 22. The process of any of clauses 12 to 17, wherein introducing the at least one of the pentose-rich stream or the hexose-rich stream to a bioreactor comprises introducing the pentose-rich stream to the bioreactor and introducing the hexose-rich stream to a second bioreactor.

Clause 23. A system for production of hydrocarbon fuels, the system comprising:
 a pretreatment system configured to treat lignocellulosic biomass;
 a first separation system coupled with to the pretreatment system;
 a hydrolysis system coupled with to the first separation system;
 a second separation system coupled with to the hydrolysis system;
 at least one bioreactor coupled with to the first separation system; and
 at least one bioreactor coupled with to the second separation system.

Clause 24. The system of clause 23, wherein the first separation system is configured to separate a pentose-rich stream from a lignocellulosic pentose-lean stream.

Clause 25. The system of any of clauses 23 to 24, further comprising a plurality of bioreactors coupled with the first separation system.

Clause 26. The system of any of clauses 23 to 25, further comprising a plurality of bioreactors coupled with the second separation system.

Clause 27. The system of any of clauses 23 to 26, wherein the lignocellulosic biomass is derived from at least one of: corn stover, switchgrass, or wheat straw.

Clause 28. The system of any of clauses 23 to 27, further comprising a sparge line coupled with the bioreactor configured to deliver at least one of air, oxygen, methanol, or ethanol to the at least one bioreactor.

Clause 29. A system for production of hydrocarbon fuels, the system comprising:
 a pretreatment system configured to treat lignocellulosic biomass;
 a first separation system coupled with to the pretreatment system;
 a hydrolysis system coupled with to the first separation system;
 a second separation system coupled with to the hydrolysis system;
 at least one bioreactor coupled with to the first separation system and the second separation system.

Clause 30. The system of clause 29, wherein the first separation system is configured to separate a pentose-rich stream from a lignocellulosic pentose-lean stream.

Clause 31. The system of any of clauses 29 to 30, further comprising a plurality of bioreactors coupled with the first separation system.

Clause 32. The system of any of clauses 29 to 31, wherein the lignocellulosic biomass is derived from at least one of: corn stover, switchgrass, or wheat straw.

Clause 33. The system of any of clauses 29 to 32, further comprising a sparge line coupled with the bioreactor configured to deliver at least one of air, oxygen, methanol, or ethanol to the at least one bioreactor.

Clause 33. A system for production of hydrocarbon fuels, the system comprising:
 a pretreatment system configured to treat lignocellulosic biomass;
 a hydrolysis system coupled with to the pretreatment system;
 a sugar separation system coupled with to the hydrolysis system; and
 at least one bioreactor coupled with to the sugar separation system.

Clause 34. The system of clause 33, wherein the sugar separation system is configured to separate a pentose-rich stream from a hexose-rich stream.

Clause 35. The system of any of clauses 33 to 34, further comprising a plurality of bioreactors coupled with the sugar separation system.

Clause 36. The system of any of clauses 33 to 35, wherein the lignocellulosic biomass is derived from at least one of: corn stover, switchgrass, or wheat straw.

Clause 37. The system of any of clauses 33 to 36, further comprising a sparge line coupled with the bioreactor configured to deliver at least one of air, oxygen, methanol, or ethanol to the at least one bioreactor.

Overall, it has been found that partial or complete separation of pentose sugars from hexose sugars before addition to a bioreactor increases efficiency and reduces costs in the production of hydrocarbon fuels and chemicals from biological sources including lignocellulosic biomass. The efficiencies created by separation of a pentose-rich stream and a hexose-rich stream are, at least, two-fold: The microorganisms convert pentose and hexose sugars at different rates and the nonconcurrent addition of different sugar types allows for more efficient bioconversion of sugars to fuels and chemicals. Additionally, the development of microorganisms useful in bioconversion systems and processes is time consuming and labor intensive and typically has relied on a single sugar in the development process; the separation of sugar streams allows for more efficient development of microorganisms capable of efficiently producing fuels and chemicals from biomass, including lignocellulosic biomass.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise whenever a composition, an element or a group of elements is preceded with the transitional phrase "comprising," it is understood that we also contemplate the same composition or group of elements with transitional phrases "consisting essentially of," "consisting of" "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed:

1. A process for producing fuel from lignocellulosic biomass, the process comprising:
    introducing biomass to a pretreatment system forming a pretreatment effluent;
    introducing the pretreatment effluent to a first separation system forming a pentose-rich stream and a pentose-lean stream;
    introducing the pentose-lean stream to a hydrolysis system forming a hydrolysate;
    introducing the hydrolysate to a second separation system forming a hexose-rich stream and a lignin stream;
    introducing the pentose-rich stream to a first bioreactor containing a first microorganism configured to produce the fuel by converting pentose into a first fatty acid ester, wherein the fuel comprises the first fatty acid ester;
    adjusting an initial feed rate of the pentose-rich stream to the first bioreactor with increase of time on stream;
    introducing the hexose-rich stream to a second bioreactor containing a second microorganism configured to produce the fuel by converting hexose into a second fatty acid ester, wherein the second microorganism is the same or different than the first microorganism and the second fatty acid ester is the same or different than the first fatty acid ester; and
    adjusting an initial feed rate of the hexose-rich stream to the second bioreactor with increase of time on stream, wherein the initial feed rate of the pentose-rich stream to the first bioreactor is different than the initial feed rate of the hexose-rich stream to the second bioreactor.

2. The process of claim 1, further comprising concentrating the pentose-rich stream to a sugar concentration of 40 wt % to 60 wt %.

3. The process of claim 1, further comprising concentrating the hexose-rich stream to a sugar concentration of 40 wt % to 60 wt %.

4. The process of claim 1, further comprising purifying the pentose-rich stream.

5. The process of claim 1, further comprising purifying the hexose-rich stream.

6. The process of claim 1, wherein the first fatty acid ester is a fatty acid methyl ester or fatty acid ethyl ester.

7. The process of claim 1, wherein introducing the pentose-rich stream to the first bioreactor comprises introducing the pentose-rich stream to the first bioreactor before introducing the hexose-rich stream to the second bioreactor.

8. The process of claim 1, wherein introducing the pentose-rich-stream to the first bioreactor comprises introducing the pentose-rich stream to the first bioreactor at an initial rate higher than an initial rate of introducing the hexose-rich stream to the second bioreactor.

9. The process of claim 1, wherein adjusting the feed rate of the pentose-rich stream to the first bioreactor comprises introducing the pentose-rich stream to the first bioreactor at a rate that declines with increase of time on stream.

10. The process of claim 1, wherein adjusting the feed rate of the hexose-rich stream to the second bioreactor comprises introducing the hexose-rich stream to the second bioreactor at a rate that increases with increase of time on stream.

11. The process of claim 1, wherein the first microorganism is an *Escherichia coli* bacteria.

12. The process of claim 11, wherein the *Escherichia coli* bacteria is a genetically modified *Escherichia coli* bacteria.

13. The process of claim 1, wherein the first microorganism is configured to form a fatty acid and transesterify the fatty acid to form the first fatty acid ester.

14. The process of claim 1, further comprising introducing a feed consisting of alcohol into the first bioreactor.

15. The process of claim 14, wherein the first bioreactor has a concentration of alcohol of about 1 wt % to about 10 wt % based on total weight of alcohol plus the pentose-rich stream.

16. The process of claim 1, wherein the hydrolysis stream comprises an enzyme configured to form the hydrolysate.

17. The process of claim 16, wherein the enzyme is a β-glucosidase.

18. The process of claim 1, wherein the pentose-rich stream and the hexose-rich stream each have a monosaccharide concentration of about 5 wt % to about 20 wt % based on the total weight of the pentose-rich stream and the hexose-rich stream respectively.

19. The process of claim 1, wherein the first microorganism comprises a fatty acid synthase.

20. The process of claim 1, further comprising introducing water to the second separation system, wherein the water is obtained from an anaerobic digestion process of waste water.

21. The process of claim 20, further comprising removing a lignin-rich stream from the second separation system, the lignin-rich stream comprising a moisture content of about 20 wt % to about 40 wt %.

22. The process of claim 21, further comprising introducing the lignin-rich stream to a steam generator to produce steam.

23. The process of claim 22, further comprising producing electricity by introducing the steam to an expander comprising an electrical generator.

\* \* \* \* \*